US011794025B1

(12) United States Patent
Shaker et al.

(10) Patent No.: US 11,794,025 B1
(45) Date of Patent: Oct. 24, 2023

(54) COMPACT AED WITH INTEGRATED CPR COACHING

(71) Applicant: ALTRIX MEDICAL, INC., Centreville, VA (US)

(72) Inventors: Matthew Robert Shaker, Centreville, VA (US); Jesse S. Kruska, Westport, CT (US); Daniel Fleck, Potomac, MD (US)

(73) Assignee: Altrix Medical, Inc., Centreville, VA (US)

( * ) Notice: Subject to any disclaimer, the term of this patent is extended or adjusted under 35 U.S.C. 154(b) by 0 days.

(21) Appl. No.: 18/077,068

(22) Filed: Dec. 7, 2022

Related U.S. Application Data

(63) Continuation-in-part of application No. 17/878,992, filed on Aug. 2, 2022, now Pat. No. 11,547,863, which is a continuation-in-part of application No. 17/712,881, filed on Apr. 4, 2022, now Pat. No. 11,433,249, application No. 18/077,068, filed on Dec. 7, 2022 is a continuation-in-part of application No. 17/969,370, filed on Oct. 19, 2022, now Pat. No. 11,633,613, which is a continuation-in-part of application No. 17/878,992, filed on Aug. 2, 2022, now Pat. No. 11,547,863, which is a continuation of application No. 17/712,881, filed on Apr. 4, 2022, now Pat. No. 11,433,249.

(51) Int. Cl.
*A61N 1/39* (2006.01)
*A61N 1/04* (2006.01)

(52) U.S. Cl.
CPC ........... *A61N 1/3904* (2017.08); *A61N 1/046* (2013.01); *A61N 1/0492* (2013.01)

(58) Field of Classification Search
CPC ..... A61N 1/046; A61N 1/0492; A61N 1/3904
See application file for complete search history.

(56) References Cited

U.S. PATENT DOCUMENTS

| | | | |
|---|---|---|---|
| 5,645,571 A * | 7/1997 | Olson | A61N 1/3931 607/142 |
| 6,125,299 A | 9/2000 | Groenke et al. | |
| 6,134,479 A | 10/2000 | Brewer et al. | |
| 8,798,743 B1 * | 8/2014 | Khuon | A61B 5/053 607/5 |
| 10,799,709 B2 * | 10/2020 | Teber | A61N 1/3968 |
| 10,953,234 B2 * | 3/2021 | Kumar | A61N 1/025 |
| 11,185,709 B2 * | 11/2021 | Kumar | A61N 1/3987 |
| 11,197,631 B2 | 12/2021 | Liu et al. | |
| 11,253,715 B2 * | 2/2022 | Kumar | A61B 5/282 |

(Continued)

*Primary Examiner* — Eric D. Bertram
(74) *Attorney, Agent, or Firm* — Louis Ventre, Jr.

(57) ABSTRACT

A compact AED with integrated CPR coaching has capability to provide coaching on cardiopulmonary resuscitation for a person in cardiac distress. The compact AED is also capable of delivering an electrical charge to the person. The AED is provided in a device body, which comes in two parts: a front-body housing and a user-separable cartridge, the latter holding disposable AED components. The front-body housing is placed on the chest of a person undergoing CPR. Use of the front-body housing enables the compact AED to coach the rescuer on CPR. One or more CPR sensors are part of the front-body housing. A circuit board within the front-body housing receives data from AED and CPR sensors and enables coaching of the rescuer.

17 Claims, 15 Drawing Sheets

(56) References Cited

U.S. PATENT DOCUMENTS

| | | | |
|---|---|---|---|
| 11,433,249 B1* | 9/2022 | Shaker | A61N 1/0492 |
| 11,547,863 B1* | 1/2023 | Shaker | A61N 1/3904 |
| 11,633,613 B1* | 4/2023 | Shaker | A61N 1/046 |
| | | | 607/5 |
| 2002/0156506 A1* | 10/2002 | Kroll | A61N 1/3975 |
| | | | 607/5 |
| 2004/0260376 A1* | 12/2004 | Craige, III | A61N 1/046 |
| | | | 600/382 |
| 2006/0155354 A1 | 7/2006 | Heath | |
| 2008/0033495 A1* | 2/2008 | Kumar | A61N 1/3968 |
| | | | 607/5 |
| 2009/0254136 A1 | 10/2009 | Powers | |
| 2010/0234908 A1 | 9/2010 | Didon | |
| 2011/0077497 A1* | 3/2011 | Oster | A61B 5/259 |
| | | | 600/300 |
| 2011/0257695 A1* | 10/2011 | Jonsen | A61B 50/31 |
| | | | 206/718 |
| 2012/0265265 A1 | 10/2012 | Razavi et al. | |
| 2013/0282072 A1 | 10/2013 | Abdeen et al. | |
| 2014/0100497 A1 | 4/2014 | Hayashi et al. | |
| 2014/0107541 A1 | 4/2014 | Sullivan et al. | |
| 2014/0277225 A1 | 9/2014 | Quan et al. | |
| 2014/0277228 A1 | 9/2014 | Quan et al. | |
| 2014/0317914 A1* | 10/2014 | Shaker | A61N 1/046 |
| | | | 29/825 |
| 2015/0045697 A1 | 2/2015 | Richard et al. | |
| 2015/0045869 A1* | 2/2015 | Albright | A61N 1/0492 |
| | | | 29/877 |
| 2015/0046175 A1* | 2/2015 | Jorgenson | A61N 1/3925 |
| | | | 705/2 |
| 2015/0273226 A1* | 10/2015 | Einy | A61N 1/3968 |
| | | | 607/6 |
| 2016/0045753 A1* | 2/2016 | Axness | A61N 1/3931 |
| | | | 607/5 |
| 2016/0095529 A1* | 4/2016 | Khuon | A61B 5/113 |
| | | | 600/509 |
| 2017/0056682 A1* | 3/2017 | Kumar | G16H 50/20 |
| 2017/0296804 A1* | 10/2017 | Kanemoto | A61N 1/0492 |
| 2017/0361120 A1 | 12/2017 | Liu et al. | |
| 2018/0169426 A1 | 6/2018 | Montague et al. | |
| 2019/0008409 A1* | 1/2019 | Kantor | A61K 9/703 |
| 2019/0022400 A1* | 1/2019 | Kumar | A61B 5/259 |
| 2020/0094044 A1* | 3/2020 | Andrews | A61B 90/98 |
| 2020/0222707 A1* | 7/2020 | Kumar | G16H 20/30 |
| 2020/0282225 A1* | 9/2020 | Kumar | A61N 1/046 |
| 2021/0213296 A1* | 7/2021 | Kumar | A61B 5/4818 |
| 2022/0134121 A1* | 5/2022 | Kumar | A61N 1/3975 |
| | | | 607/7 |

\* cited by examiner

COMPACT AED WITH INTEGRATED CPR COACHING

CROSS-REFERENCE TO RELATED APPLICATIONS

This application is a continuation-in-part of prior U.S. application Ser. No. 17/878,992, filed 2 Aug. 2022, now U.S. Pat. No. 11,547,863, issued 10 Jan. 2023, which is a continuation of U.S. application Ser. No. 17/712,881, filed 4 Apr. 2022, now U.S. Pat. No. 11,433,249, issued 6 Sep. 2022, and this application is a continuation in part of U.S. application Ser. No. 17/969,370, filed 19 Oct. 2022, now U.S. Pat. No. 11,633,613, issued 25 Jan. 2023, which is a continuation-in-part of prior U.S. application Ser. No. 17/878,992, filed 2 Aug. 2022, now U.S. Pat. No. 11,547,863, issued 10 Jan. 2023, which is a continuation of U.S. application Ser. No. 17/712,881, filed 4 Apr. 2022, now U.S. Pat. No. 11,433,249, issued 6 Sep. 2022, all of which are hereby incorporated by reference herein in their entireties.

TECHNICAL FIELD

In the field of light, thermal, and electrical application, a device for applying electrical energy to the external surface and inside portions of the body to restore normal operation of the heart.

BACKGROUND ART

Cardiopulmonary resuscitation (CPR) is a lifesaving technique widely practiced each year. Chest compression, sometimes referred to as artificial circulation, is done by pumping the chest to circulate oxygenated blood throughout the body. Typically, CPR should be performed if a patient is non-responsive and not breathing and an Automated external defibrillator (AED) should be used in conjunction with performing CPR. While CPR keeps blood flowing to a patient's heart and brain, an AED can restore the heart's rhythm in certain situations. When a person has suffered cardiac arrest, prompt CPR and defibrillation are critical to that person's survival. Providing such immediate response, even prior to arrival by emergency personnel, can save lives.

Four factors in CPR chest compressions are often considered important to the overall technique: hand placement, depth of compression, compression rate, and chest compression fraction (CCF). The purpose of hand placement, or landmarking, is to target compressions to the most effective area of the chest while minimizing injury.

Chest compression fraction (CCF) is defined as the proportion of time that chest compressions are performed during a cardiac arrest. However, pauses in administering CPR to a person in cardiac distress are often necessary to assess that person's condition using an ECG. Recent studies have shown that such pauses are correlated with a decreased survival rate for such person or victim. Conversely, the ability to collect and analyze a cardiac arrest victim's ECG without pausing CPR is correlated with higher CCF and improved outcomes.

The International Electrotechnical Commission (IEC) is a worldwide organization for standardization comprising all national electrotechnical committees (IEC National Committees). The object of IEC is to promote international co-operation on questions concerning standardization in the electrical and electronic fields. The IEC publishes a standard for Medical electrical equipment at Part 2-4: Particular requirements for the basic safety and essential performance of cardiac defibrillators IEC 60601-2-4, which discusses requirements for the basic safety and essential performance of cardiac defibrillators. Among other things, it specifies requirements for the defibrillator electrodes. This governing standard is used to develop and package pads for defibrillators.

The compact automated external defibrillator disclosed herein is a unique and improved way to implement and package electrodes that are compliant with this standard (with the possible exception of cord length, which may be less than the standard but such new length is justified by the fact that the improvements discussed herein enable the automated external defibrillator (AED) pads to be in closer proximity to the device body when used as compared to other AEDs).

A typical AED uses two electrodes, each with a conductive gel to help transfer an AED shock to a patient. The standard calls for the minimum active gel area of self-adhesive electrodes to measure a total of 150 square centimeters, with each area being at least 50 square centimeters for adults. Pediatric pads are required to total 45 square centimeters, with each area being at least 15 square centimeters (when pediatric electrodes are used).

Most AEDs today have electrodes that are the same size and package these pads either in the AED or the AED carrying case. The electrodes are typically in a pouch but there are other packaging methods. When the AED is used, the pouch is removed from the AED or AED case and opened. A protective layer is peeled from the electrode, revealing an adhesive layer. The adhesive is electrically conductive and typically a hydrogel formula. The electrodes are adhered to the patient in specified locations.

This application discloses a fast and efficient means for coaching CPR performance and defibrillator usage during a cardiac event. This capability is added to the compact AED.

This capability is provided by attaching one or more new sensors that are part of the compact AED. These sensors are placed on the patient's chest in a way that allows CPR depth and rate to be monitored and assessed and to allow audio and/or video coaching to enhance CPR performance during administration of CPR. Haptic feedback through the front front-body housing may also be used for coaching. These sensors also allow for CPR compressions to be redacted from the electrocardiogram, providing for fewer pauses during CPR (i.e., higher CCF) and better associated clinical outcomes.

SUMMARY OF INVENTION

A compact automated external defibrillator (AED) is provided with added capability to provide coaching on cardiopulmonary resuscitation (CPR) for a person in cardiac distress. The compact AED is also capable of delivering an electrical charge to the person and redacting CPR artifacts from an electrocardiogram (ECG).

The compact automated external defibrillator is provided in a device body, which comes in two parts: a front-body housing and a user-separable cartridge, the former holding CPR sensors and the latter holding disposable AED components. During a cardiac emergency, the front-body housing is placed, center chest, on a person undergoing CPR. Use of the front-body housing enables the compact AED to coach the rescuer on CPR.

One or more CPR sensors are part of the front-body housing and electrocardiogram sensors are stored in the user-separable cartridge. Each CPR sensor measures and reports on CPR being performed on the person. The sensors preferably measure acceleration of a person's chest, force applied to the person, and the pressure applied to the person.

A circuit board within the front-body housing receives data from AED, ECG sensors and CPR sensors and enables CPR performance improvement to benefit the person in cardiac distress. CPR performance improvement includes CPR coaching of the rescuer; CPR signal redaction for improved electrocardiogram analysis; and robot synchronization of heart pumping, when a robot CPR device is available.

The circuit board calculates rate of CPR and depth of CPR using data from the sensor. A speaker connected to the circuit board enables oral instruction to the rescuer on CPR administration. The circuit board also redacts the CPR compression artifacts from an electrocardiogram using data from the sensor.

An inner wall of the front-body housing is used to secure the user-separable cartridge to the front-body housing and also to secure the circuit board within the front-body housing. There are preferably two or more electrical terminals defined on this inner wall, which are used to connect to the circuit board and to power the AED electrodes. If needed, these terminals are accessible upon removing the user-separable cartridge from the device body.

The user-separable cartridge may hold one or more of an AED proximate pad; a liner; an AED first-distal pad; an AED first-distal electrode; an AED second-distal electrode; an AED first distal-foam pad; and AED second distal-foam pad; two or more separated cartridge terminals defined on a second wall, which electrically connect to a corresponding terminal in the front-body housing. The AED proximate pad is preferably attachable to the AED second-distal electrode when that AED second-distal electrode is present. This allows the AED proximate pad to attach the user-separable cartridge and front-body housing to the person. In a different configuration, it also allows the AED proximate pad and AED second-distal electrode assembly to be removed from the user-separable cartridge, providing the ability for the user-separable cartridge and front body housing to rest on a person's chest independent of the AED proximate pad and AED second-distal electrode assembly. When child-specific AED pads are not available or provided for an AED, AED electrode placement for a child is typically center of chest and center of posterior and adult placement is typically under a person's right clavicle and on a person's left side, these different configurations permit CPR coaching and defibrillation of both adults and children. AED electrodes may be electrocardiogram sensors when attached to a person.

Technical Problem

A frequent challenge for untrained responders to a sudden cardiac arrest is helping them understand what to do, how to do it, and (sometimes as important) what not to do. Even trained first responders could find real time CPR feedback helpful during an emergency. In fact, research has shown that variability in CPR performance results in poorer outcomes, a problem exacerbated by the fact that the quality of CPR typically diminishes over time due to rescuer fatigue.

Audio and video prompts, such a CPR metronome provided by an AED or even 911 assisted coaching, doesn't always provide the detail needed because real time data cannot be assessed. This can be especially problematic with CPR where rate and depth of compressions are particularly important along with limiting pauses to CPR (increased chest compression fraction).

Simultaneous electrocardiograms (ECG) taken of patients undergoing cardiopulmonary resuscitation (CPR) can lead to contamination of the CPR frequency data.

Contamination of the CPR frequency data inhibits the development of correct guidance being given to the rescuer on recommendations for defibrillation or on synchronizing chest compressions with residual activity in the heart.

Contamination of ECGs can lead to incorrect analysis of the ECG for evaluating cardiac recovery of the person being treated.

A method is needed to separate out unwanted frequency data from either the ECG frequency signals or the CPR frequency signals when simultaneous electrocardiograms (ECG) are taken of patients undergoing cardiopulmonary resuscitation (CPR). Such a method should not decrease chest compression fraction.

AED electrode positioning for a child in cardiac distress is an electrode on the center chest and an electrode on the child's back. However, placement of the proximate electrode on the child's center chest using the front-body housing of the compact AED would adversely affect the administration of CPR by a rescuer.

AEDs are often too large for convenient transport and use. Adding to this problem is cord storage. According to the IEC 60601-2-4 standard, each cord leading from the AED device and ending at a pad should be least 1 meter. Most AEDs today have two pads that are the same size, which are typically packaged with the AED or are in an AED carrying case. Also, typical pads are packaged within a sealed pouch or tray. When the AED is needed for use, the pouch or tray is opened and the pads within are connected to the AED (if not pre-connected) and then attached to the patient.

The typical pads are composed of a foam backing and an electrode that have a protective layer or liner that is peeled from the pad, revealing an adhesive layer for placement on the patient. The pad is usually coated with hydrogel, which is electrically conductive. The pads are adhered to the patient in requisite locations with the hydrogel or other adhesive gel on the patient's skin.

A challenge to storing pads for most AEDs involves the conductive material on the metal surface, typically a hydrogel formula. These formulas typically require special storage to minimize exposure to air in order to keep the hydrogel from drying out (i.e., reduce evaporative drying), thereby extending the shelf life of the electrode pads.

Solution to Problem

The solution to enable both CPR coaching and defibrillation is to add CPR sensors to the front-body housing of the compact AED, and then attach that front-body housing to the center chest of the person in cardiac distress.

A first solution addressing child CPR and automated external defibrillation is a compact AED with a second-distal electrode that is electrically connected to the proximate terminal on the front-body housing and attached to a proximate pad. This configuration allows the front-body housing to be attached to the chest of the child for administrating CPR, redacting CPR signal artifacts from an ECG obtained from the electrode pads, and enabling two distal pads to be attached to the child for defibrillation in a preferred front to back configuration used when pediatric pads are unavailable. Such a configuration also supports adult defibrillation by allowing the proximate pad to be removed and attached in a location other than beneath the front AED housing that is used for CPR coaching and CPR signal redaction from an ECG. In the event of proximate pad removal, a preferred embodiment would include additional adhesive to adhere the AED body to the patient once the proximate pad is removed.

A second solution addressing child CPR and automated external defibrillation is enabling the proximate electrode on the inner wall of the front-body housing to connect to both a proximate pad and a second distal pad. This configuration would allow the front-body housing to utilize the CPR sensors and also be used for defibrillation. Such a solution also offers an alternative configuration for adult defibrillation and CPR data by allowing for placement of the first distal pad and second distal pad in a location other than beneath the front AED housing that is used for CPR coaching and CPR artifact redaction from an ECG obtained from the electrode pads.

A third solution addressing child CPR and AED administration is adding a third terminal on the inner wall of the front-body housing to allow connection to a second-distal electrode. This third terminal would be independent of both the proximate electrode and the connecting electrode for the first distal electrode. This configuration also allows the front-body housing to be attached to the chest for administrating CPR and enabling two distal pads to be attached in configurable locations for defibrillation.

The compact automated external defibrillator minimizes space required to store the pads with the AED by using these alternative configurations.

The solution seals the compact automated external defibrillator from air infiltration to protect the pads from drying out.

The solution of adhering the AED device to the patient is desirable because the compact automated external defibrillator is small and attaching it ensures that the AED is stable and does not "fly around" during the rescue event. Adhering the AED device to the patient limits possible injuries to the patient or bystanders and also provides added confidence that the electrical connections are maintained.

Advantageous Effects of Invention

The solutions disclosed herein enables CPR coaching and defibrillation while minimizing the physical volume required to store the pads with the AED. It also allows for the redaction or reduction of CPR artifacts in an ECG.

One solution disclosed herein employs an alternative configuration for the compact AED where the compact AED attaches to the person (the patient) and requires only one remote pad for defibrillation.

Another solution disclosed herein employs an alternative configuration for the compact AED where the compact AED attaches to the patient and two distal electrodes are attached to the person. This is accomplished with either three terminals on the front-body housing or having the proximate electrode on the front-body housing electrically connected to a second-distal electrode, acting as either the proximate electrode or as a second-distal electrode.

The solution enables spooling and shortening the electrical wires or cords that connect to AED distal pads. Spooled and shortened wires help to minimize storage space, maximize efficiency in deployment, and reduce cost. Cords used in the compact AED could be shorter than a meter because the AED front-body housing would be in the middle of a patient's chest. On existing, non-compact AEDs, cords are usually a meter long, which is a drawback associated with storage and a difficulty involving tangling, which hampers efficiency. A reduced wire length also reduces electrical noise picked up by the wire and decreases impedance between the patient and the front-body housing.

The preferred solution disclosed herein strives to minimize duplication of component parts within the AED to provide an AED operable with fewer component parts than AEDs heretofore available.

The solution disclosed herein provides a reusable AED once the pads are replaced, which reduces replacement costs and adds to functionality.

The solution disclosed herein extends the life of the AED by allowing hydrogel, or other adhesive, to be replaced prior to or after expiration.

This solution enables the use of pads having different sizes, and complies with IEC60601-2-4 requirements for total area and minimum individual area.

These solutions preferably utilize two separate and reusable terminals defined on the wall of the front-body housing, one terminal being the proximate electrode and the other terminal being the connecting electrode.

BRIEF DESCRIPTION OF DRAWINGS

The drawings illustrate preferred embodiments of the compact AED with integrated CPR coaching according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

Figure 1:
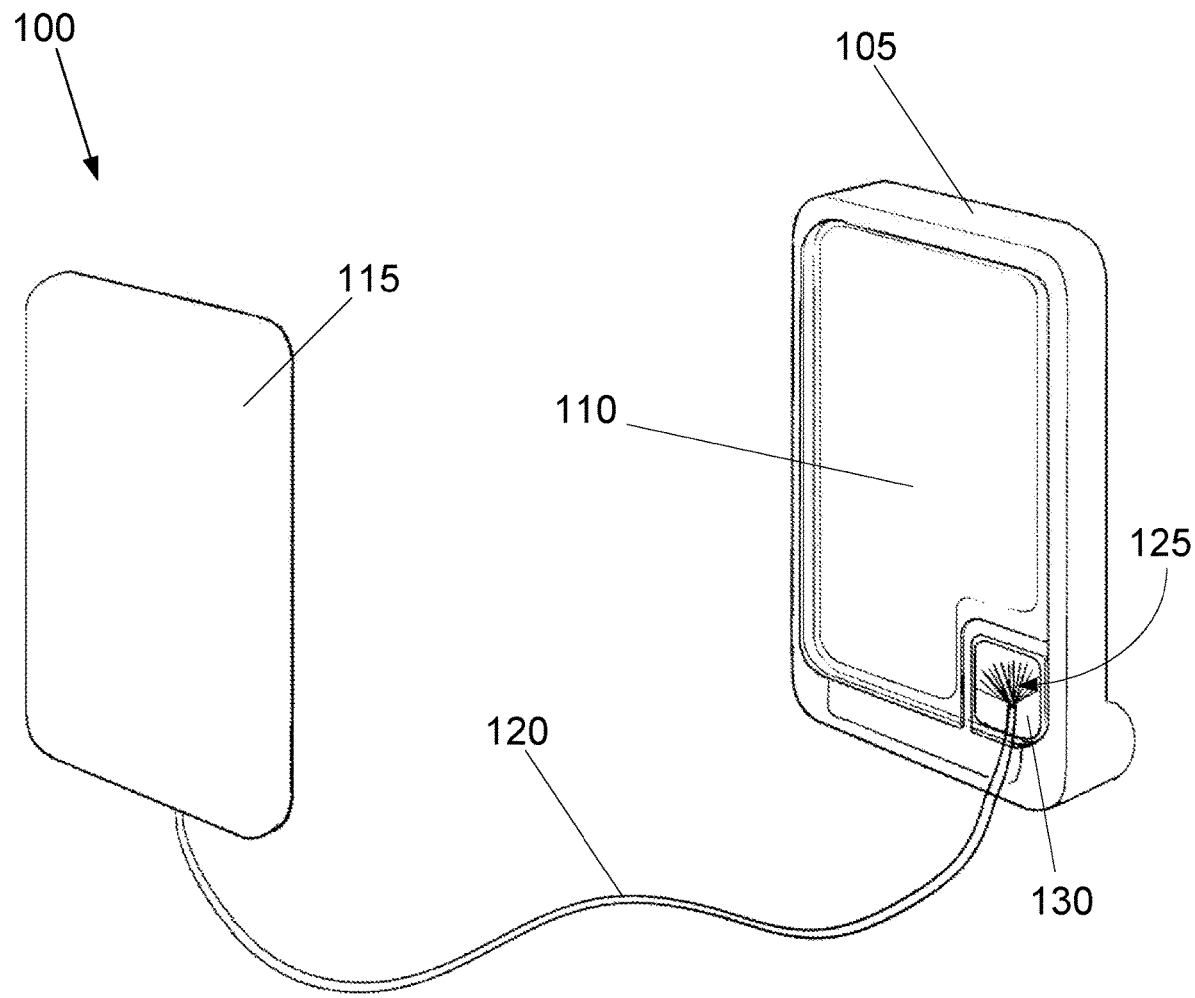
FIG. 1 is a perspective of a first embodiment showing the AED first distal electrode separated from the front-body housing.

In the following description, reference is made to the accompanying drawings, which form a part hereof and which illustrate several embodiments of the Compact AED With Integrated CPR Coaching as disclosed herein. The drawings and the preferred embodiments of the Compact AED With Integrated CPR Coaching are presented with the understanding that the Compact AED With Integrated CPR Coaching is susceptible of embodiments in many different forms and, therefore, other embodiments may be utilized and structural, and operational changes may be made, without departing from the scope of the present invention.

In one embodiment, the compact automated external defibrillator (100) is configured to provide coaching on cardiopulmonary resuscitation (CPR) for a person (601) in cardiac distress and further configured to deliver an electrical charge to the person (601) when defibrillation is necessary.

The compact automated external defibrillator (100) is considered compact because it comes in a package or device body (105) that is about one inch thick by about 3.75 inches wide and about 7 inches long. In other words, it is larger than a mobile phone and small enough to be carried in one's pocket.

The device body (105) is compartmentalized into two compartments that include a front-body housing (445) and a user-separable cartridge (1315). A handle (1355) at the rear of the user-separable cartridge (1315) may be used to remove a packing cover (455) and then unpack the user-separable cartridge (1315) while the user-separable cartridge (1315) remains electrically connected to the front-body housing (445).

The front-body housing (445) holds parts considered to be usable over and over again, while the user-separable cartridge (1315) holds parts that are considered user replaceable once they have served their purpose in defibrillating one or more persons in cardiac distress. Essentially, the user-separable cartridge (1315) includes AED components that are disposable after use. In one embodiment, the user-separable cartridge is wholly replaceable.

The front-body housing (445) is configured to be used for CPR performance improvement. CPR performance improvement includes CPR coaching of the rescuer; CPR signal redaction for improved electrocardiogram analysis; and robot synchronization of heart pumping, when a robot CPR device is available.

The front-body housing (445) is laid center chest, near the person's heart and the rescuer's hands are then placed atop the front-body housing (445) when CPR is performed. The front-body housing (445) also contains the reusable components needed for CPR performance improvement and for defibrillation. Prior to defibrillation, the AED preferably takes an ECG of a person. The re-usable CPR components may be used to redact or limit the CPR artifacts that may show up in an ECG during CPR.

The front-body housing (445) includes a front surface (1305), which essentially is the front of the device body (105); a sensor (1310) to gather data for CPR performance improvement; a circuit board (415); a speaker (1415); a wall (1505); and at least two separate and reusable terminals (1345) used to electrically connect to the AED electrodes. Any terminal in the front-body housing (445) or the user-separable cartridge (1315) is an electrical terminal that may have any known terminal configuration, such as a flat profile, a recessed design, a projecting design, snap on, and/or plug in.

The battery (450) is preferably located in the front-body housing (445), but may be located in the user-separable cartridge (1315), or may have a flat-packed design in either location.

The front surface (1305) is the exterior face of the outer wall of the front-body housing (445), which is also an exterior wall of the device body (105). The sensor (1310) is preferably mounted on, within or to the front surface (1305) of the front-body housing (445) and is operable when the front-body housing (445) is placed near the center of the person's chest.

The sensor (1310) is configured to measure CPR parameters. The sensor (1310) is configured for operability when the front surface (1305) is laid, facing up or facing down, atop the person (601), but preferably on the chest of the person (601).

The sensor (1310) is integrated into the front-body housing (445). Preferably, the sensor (1310) is configured to be operable when the front surface (1305) and the front-body housing (445) is laid on the person's skin near the heart so that when CPR is administered, the sensor (1310) detects and reports on CPR performance including, at least one of the following: chest compression fraction; chest compression rate; chest compression depth; chest recoil; and ventilation. Coaching encompasses feedback to the rescuer to help minimize interruptions in chest compressions, to ensure compressions of adequate rate and depth, to alert the rescuer when chest recoil or residual leaning is detected between compressions, and to avoid excessive ventilation of the person (601) undergoing CPR. Coaching preferably includes visual and/or auditory feedback on rate and depth. Such feedback may be on the AED and/or on an external device, such as a smartphone or other wirelessly connected display or device.

The compact AED enables integration with a CPR robot. A CPR robot is essentially an automated chest compression device that can automate CPR on the person being rescued. The CPR robot is configured to sense CPR depth and rate and also to use that information to redact CPR artifacts when taking an electrocardiogram (ECG). The CPR robot utilizes a piston that pushes the person's chest. This piston would be configured to integrate with the front-body housing (445). The CPR robot may also integrate with the circuit board (415) in a wired or wireless configuration. The CPR robot may also use the AED to obtain an ECG and use that ECG to synchronize chest compressions with residual heart activity to make the CPR more effective.

One or more sensors may be included, but are referred to in the singular herein. The sensor (1310) may include an inertial measurement unit (IMU), which is an electronic device that measures and reports a body's specific force, angular rate, and sometimes the orientation of the body, using a combination of accelerometers, gyroscopes, and sometimes magnetometers.

The circuit board (415) is an indivisible unit. An indivisible unit essentially means that the circuit board (415) may not be physically broken apart to provide circuit board functionality in another part of the AED, such as in a distal electrode. There may be one or more circuit boards, but none of these that may be physically separated or divided into two or more such boards. The circuit board (415) is configured to receive data from the sensor (1310) and the AED electrodes, and also to operate the AED to deliver a defibrillation electrical charge when called upon at the appropriate time. The circuit board (415) is preferably configured to enable the AED to wirelessly integrate with an external computer, a smartphone app, or with the cloud via the Internet.

The wall (1505) is an interior part of the front-body housing (445) that secures the circuit board (415) within the front-body housing (445). The wall (1505) only becomes visible and accessible when the front-body housing (445) is separated from the user-separable cartridge (1315). The wall (1505) may be a solid wall enclosure or the wall (1505) may be a partial enclosure, for example to permit air circulation and cooling of the circuit board (415).

The wall (1505) defines at least two separate and reusable terminals (1345) that are electrically connected to the circuit board (415). The at least two separate and reusable terminals (1345) are used for making electrical connections for AED electrodes, and are termed the proximate electrode (110) and the connecting electrode (130). The AED electrodes are configured for use in delivering an electrical charge for defibrillation and for obtaining an ECG from the person (601). The at least two separate and reusable terminals (1345) become accessible upon removing the user-separable cartridge (1315) from the front-body housing (445). The at least two separate and reusable terminals (1345) may be used to take an ECG with or without the user-separable cartridge (1315).

Figure 13:
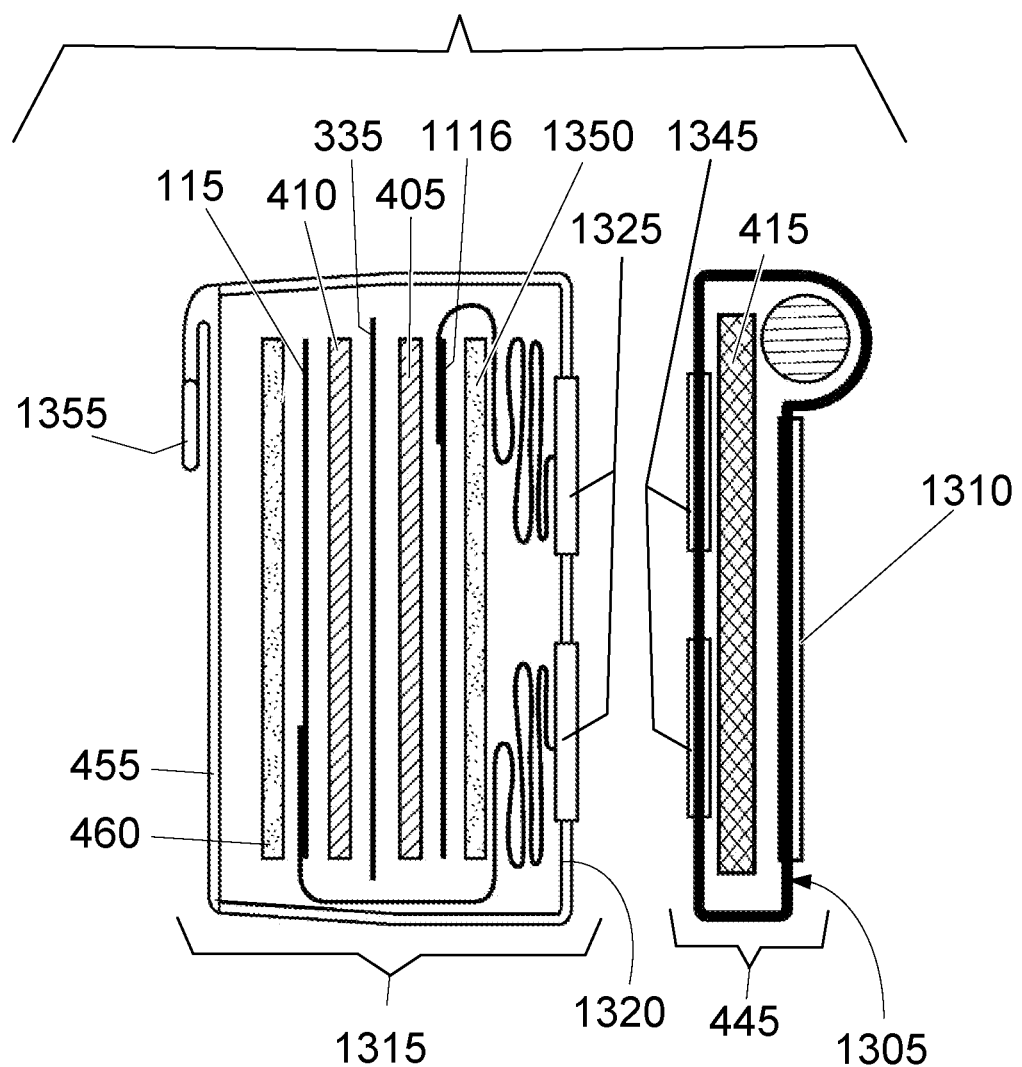
FIG. 13 is an exploded view of the preferred alternative embodiment of the compact AED with integrated CPR coaching.
Figure 14A:
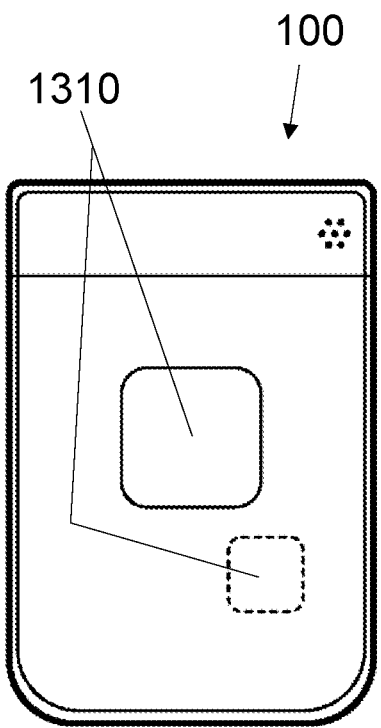
FIG. 14A is a front view of the preferred alternative embodiment of the compact AED with integrated CPR coaching showing CPR sensor locations.
Figure 14B:
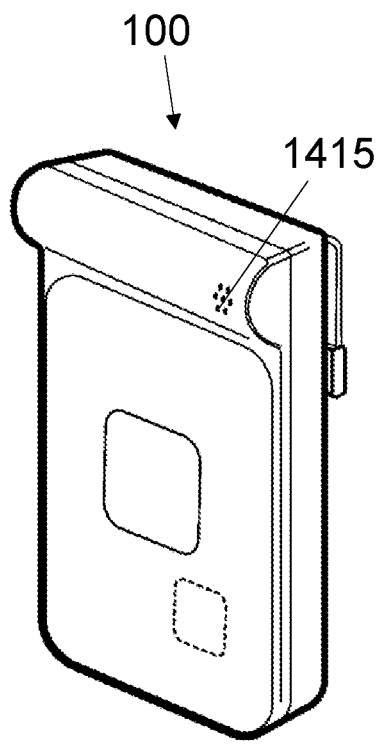
FIG. 14B is a perspective view of the embodiment of FIG. 14A.
Figures 15, 16:
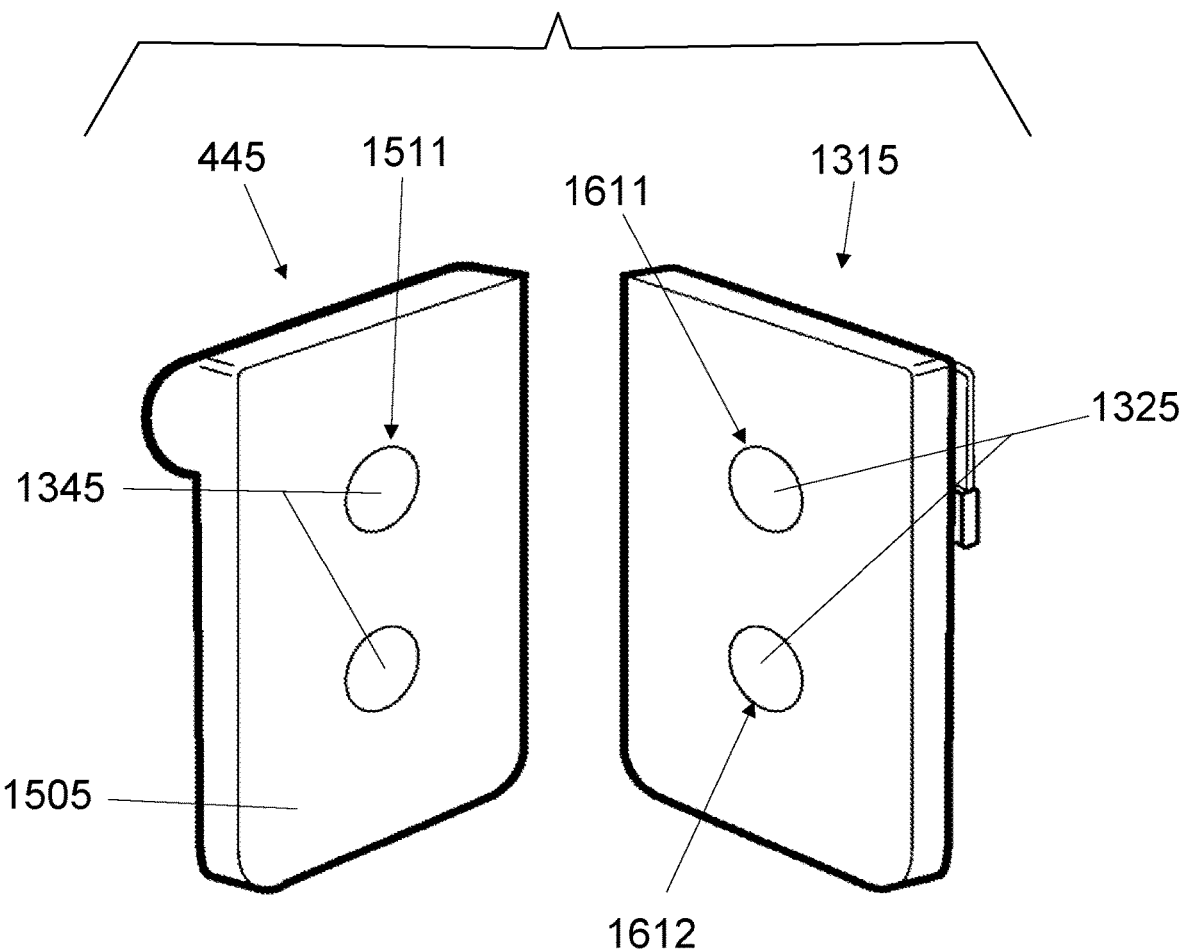
FIG. 15 is a perspective view of the front-body housing of the embodiment of FIG. 14A showing two terminals located on an inner wall of the front-body housing.
FIG. 16 is a perspective view of the user-separable cartridge of the embodiment of FIG. 14A showing two mating terminals located on a second wall of the user-separable cartridge.

AED components in the user-separable cartridge (1315) shown in FIG. 13 may include: an AED proximate pad (405); a liner (335); an AED first-distal pad (410); an AED first-distal electrode (115); an AED second-distal electrode (1116); and at least two separated cartridge terminals (1325) defined on a second wall (1320). Each of the at least two separated cartridge terminals (1325) in the user-separable cartridge (1315) are configured to electrically connect to one of the at least two separate and reusable terminals (1645) on the wall (1505) in the front-body housing (445), that is, when only two of the at least two separated cartridge terminals (1325) are present, to electrically connect to either the proximate electrode (110) or the connecting electrode (130).

The AED first-distal electrode (115) is electrically connected to a first (1611) of the at least two separated cartridge terminals (1325) in the front-body housing (445).

The user-separable cartridge (1315) may include an AED second-distal electrode (1116) that is configured for attachment to the AED proximate pad (405). Optionally, the AED second-distal electrode (1116) is electrically connected to a second (1612) of the at least two separated cartridge terminals (1325) in the user-separable cartridge (1315).

The AED proximate pad (405) may be electrically connected to the AED second-distal electrode (1116), so that it may be used for defibrillation of a child where electrodes are placed on the front and back of the child. This option permits use of the CPR sensors in addition to the two AED electrodes.

The AED proximate pad (405) may be configured to attach the user-separable cartridge (1315) to the person (601). This option permits use of both the front-body housing (445) for CPR performance improvement and the user-separable cartridge (1315) for an AED electrode. It also allows the user-separable cartridge (1315) to be used as an AED electrode without the benefit of CPR enhancements, for example attachment to an adult at an area not near the center of the chest (e.g., placed under the right clavicle or on left side of a person).

Figure 11:
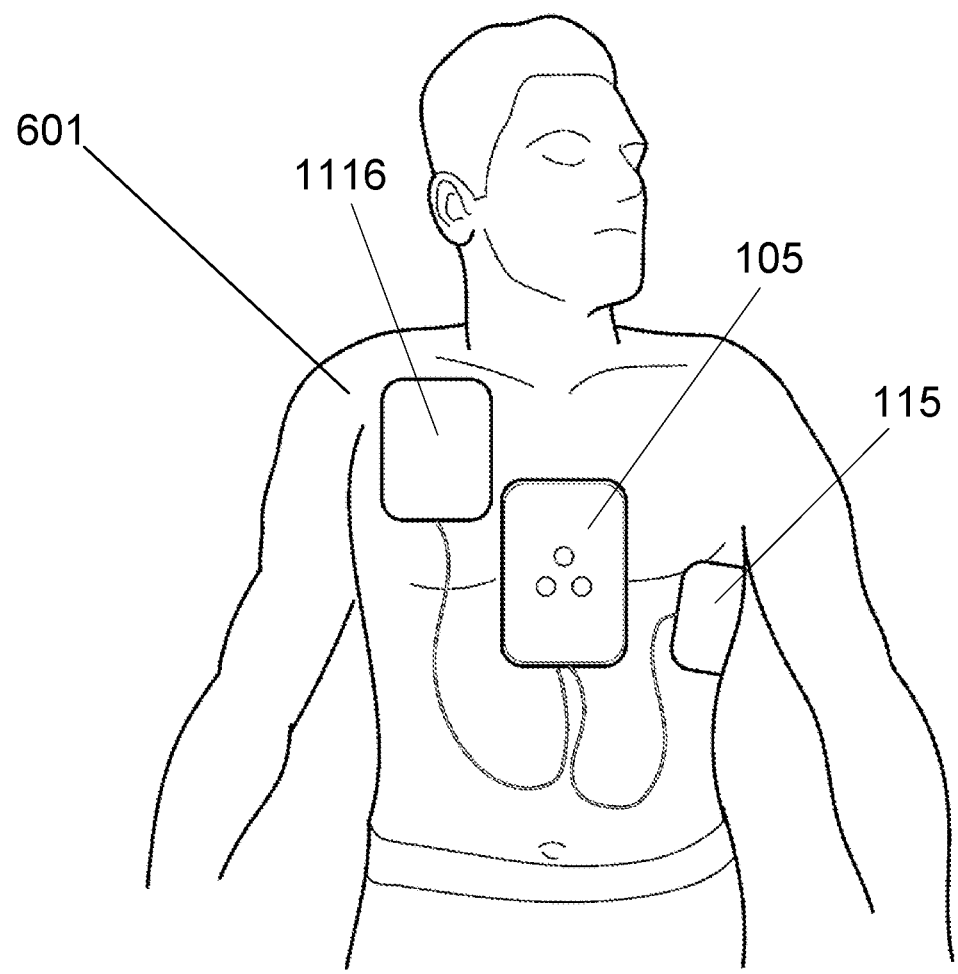
FIG. 11 is a top view of the compact AED with integrated CPR coaching deployed on a person being treated.
Figures 12A, 12B:
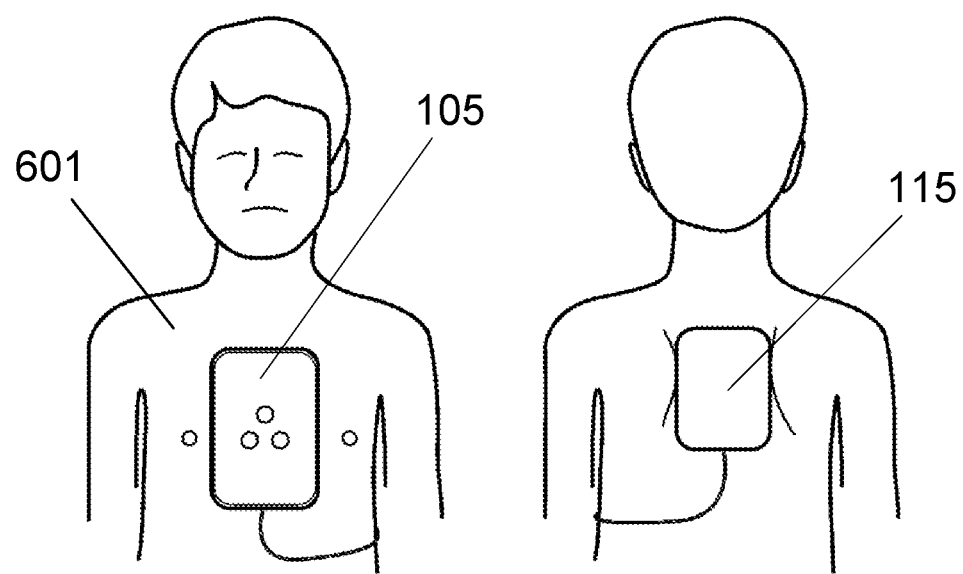
FIG. 12A is a front view of the compact AED with integrated CPR coaching deployed on a child being treated.
FIG. 12B is a rear view of the compact AED with integrated CPR coaching deployed on a child being treated.

The AED proximate pad (405) may be configured for removal from the user-separable cartridge (1315) while maintaining an electrical connection to a first (1611) of the at least two separate and reusable terminals (1345). The AED proximate pad (405) may be further configured for attachment to the person (601) to enable electrical current flow between the AED proximate pad (405) and the person (601). For example, such a configuration may be accomplished by attaching the AED proximate pad (405) to the AED second-distal electrode (1116), which would support CPR performance improvement and AED electrode attachment to an adult (see FIG. 11).

The user-separable cartridge (1315) may further include a packing cover (455). Preferably, a handle (1355) is available to pull the packing cover (455) off the user-separable cartridge (1315) so that the AED electrodes and associated pads may be easily accessed and deployed.

The user-separable cartridge (1315) is preferably disposable and is configured for replacement. The user-separable cartridge (1315) may be constructed of a rigid material such as injection molded material or a soft material to form a pouch-like structure.

The user-separable cartridge (1315) may further include an AED second distal-foam pad (1350), when the AED second-distal electrode (1116) is present. Both the first distal-foam pad (460) and the AED second distal-foam pad (1350) are one side of each AED distal defibrillation pad assembly. The first distal-foam pad (460) and the AED second distal-foam pad (1350) are also useful in helping to hold in-place wires electrically connecting the AED distal electrodes to the circuit board (415). They are further useful in preventing placement of a bare electrode on a person's chest. To preserve the low profile of the compact AED and to diminish tangling potential, any wire connecting within the user-separable cartridge (1315) would preferably be wrapped around a thin spool.

Preferably, the AED second-distal electrode (1116) would be connected to the proximate electrode (110) on the front-body housing (445) and used with the AED first-distal electrode (115) for defibrillation. The AED second-distal electrode (1116) is optionally available for placement on a child to be given a defibrillation shock. This permits the front-body housing (445) to be used, center chest, for administering CPR and for CPR reporting and coaching while the child is prepared to receive a defibrillation shock. Similarly, CPR coaching and reporting may be provided to an adult by removing the AED proximate pad (405) and attaching it either below the right clavicle, on the left side of the adult, or any other location preferred for adult defibrillation.

The sensor (1310) may be configured to measure acceleration of a person's chest and to measure force applied to the person (601). CPR sensors allow the rescuer to monitor the quality of resuscitation, provide data useful in coaching the rescuer about the basic parameters of the manual chest compressions being performed, and may record CPR data for later review and assessment. The compact AED may also record ECG and defibrillation data for after action review and training. Preferably, the sensor collect data on chest compression rate and depth, and full chest recoil. For example, a force measurement sensor is available that is thin and flexible. CPR sensors may also be used to allow CPR to continue while the AED takes an ECG of the person. In this case, these sensors can be used to help redact the CPR artifacts from the ECG so that an arrythmia assessment can be correctly obtained.

A first (1511) of the at least two separate and reusable terminals (1345) may be the proximate electrode (110). When this is the case, the AED second-distal electrode (1116) is preferably connected to this first (1511) of the at least two separate and reusable terminals (1345) so that it may be used for defibrillation when the person (601) is a child. A second (1612) of the at least two separate and reusable terminals (1345) may then be the connecting electrode (130) for connection to the AED first-distal electrode (115). This frees up the front-body housing (445) to be used for administration of CPR.

The circuit board (415) may be configured for defibrillation, further configured to calculate rate of CPR using data from the sensor (1310), and further configured to calculate depth of CPR using data from the sensor (1310).

A speaker (1415) may be connected to the circuit board (415). The circuit board (415) may be further configured to provide instruction through the speaker (1415) using data from the sensor (1310).

The circuit board (415) may be configured to redact CPR compression artifacts from an electrocardiogram using data from the sensor (1310). The circuit board may also include wireless connectivity such as BLUETOOTH and may be connected to a wired external interface in the housing, such as a USB plug.

Figure 4:
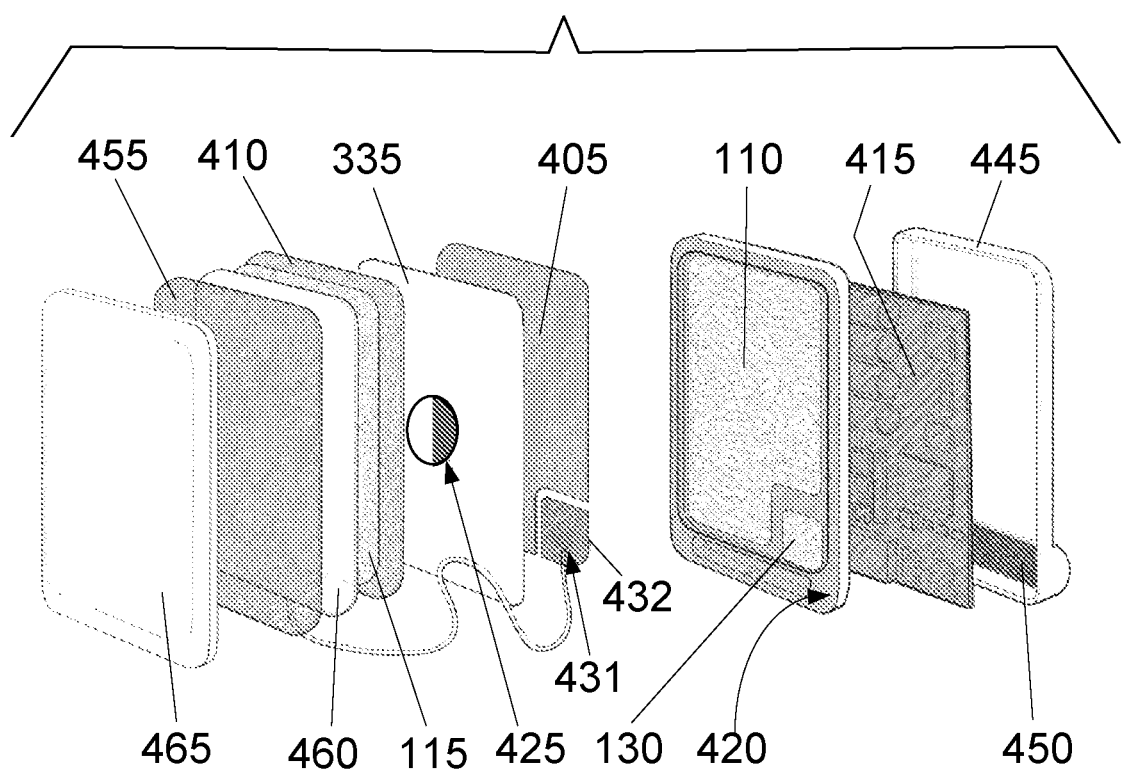
FIG. 4 is an exploded view of the first embodiment of the compact AED with integrated CPR coaching having one distal electrode.
Figure 5:
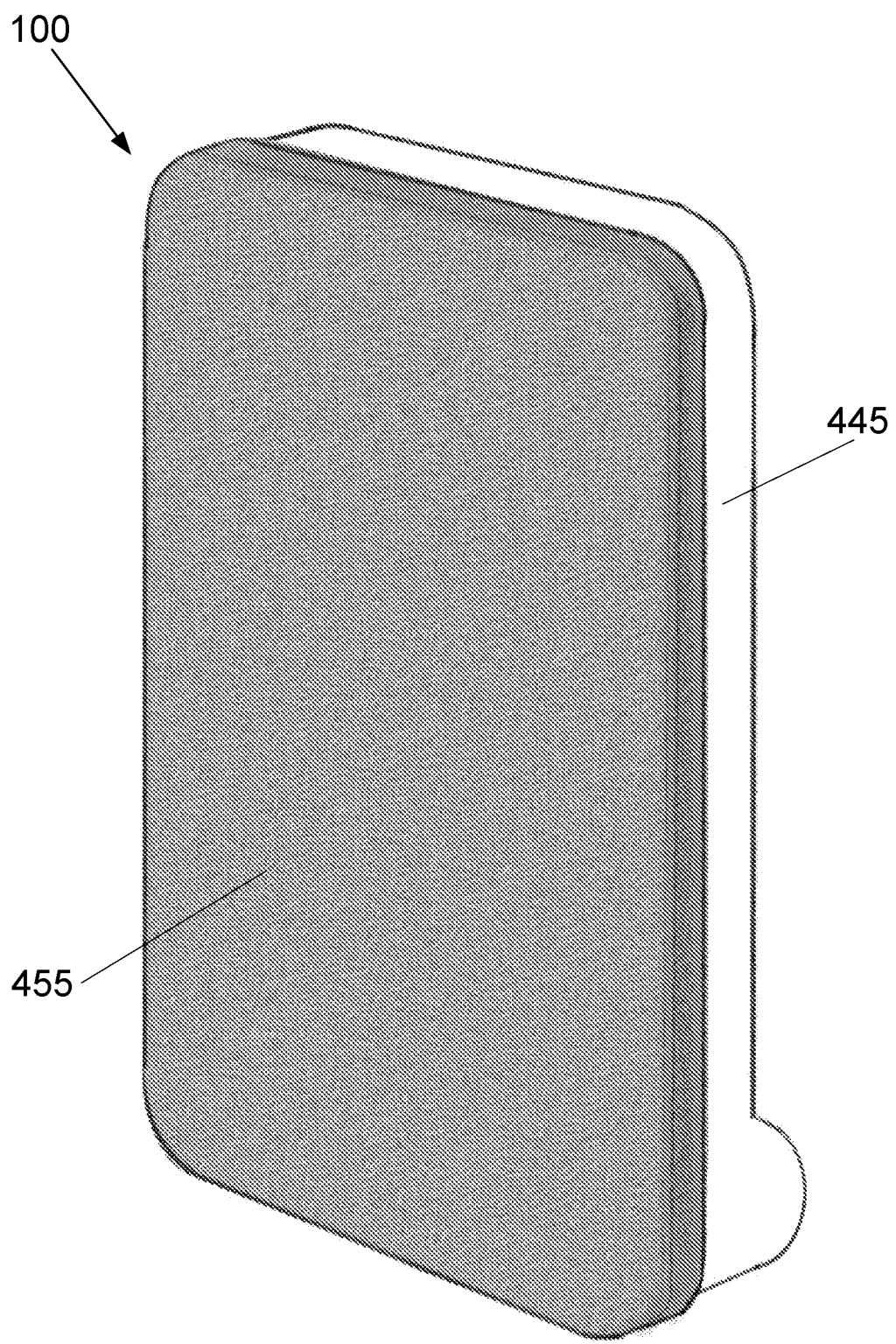
FIG. 5 is a perspective view of the rear of the first embodiment of the compact AED with integrated CPR coaching.
Figure 6:
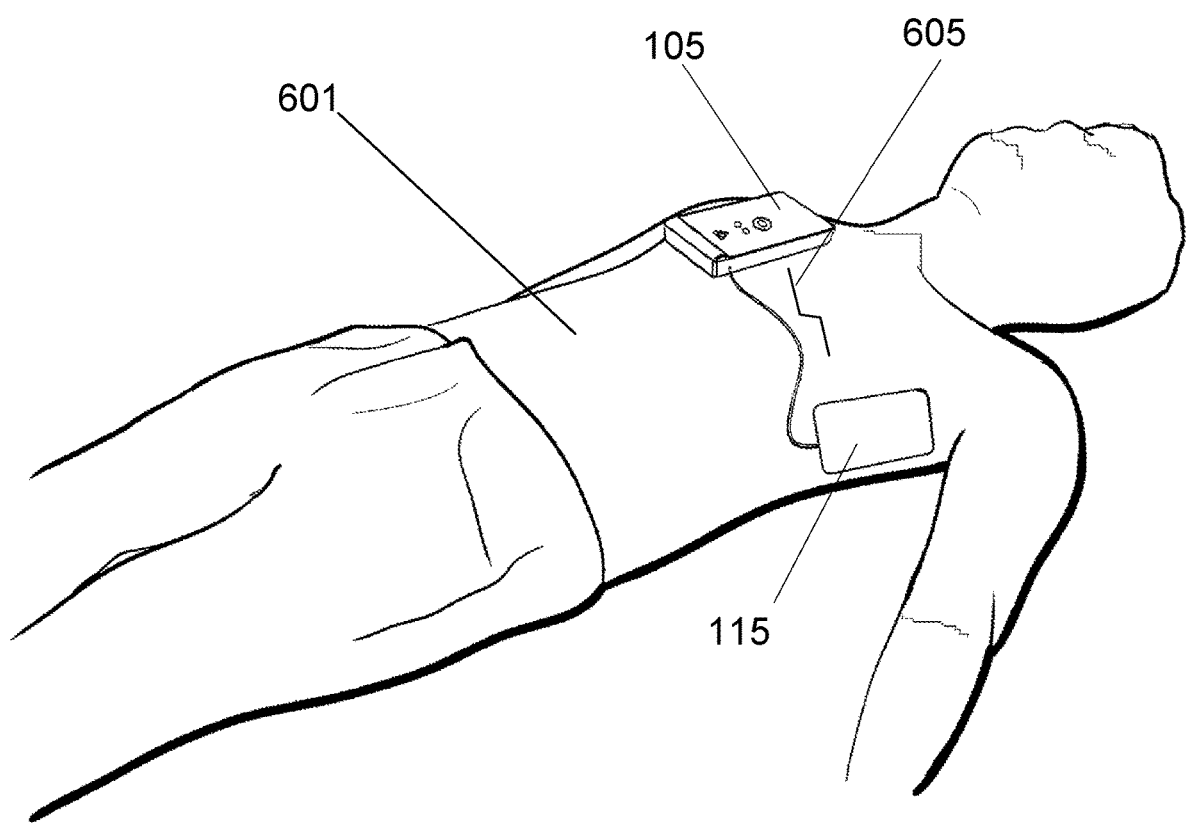
FIG. 6 is a perspective view of a person in cardiac distress showing placement of the compact AED when no CPR is to be administered to the person.

FIG. 1 is a front perspective view of the compact automated external defibrillator (100) with an AED first-distal electrode (115) shown separated from its storage position in the device body (105). The compact automated external defibrillator (100) may be referred to herein as the AED. FIG. 4 shows an exploded view of important components of the compact automated external defibrillator (100).

The compact automated external defibrillator (100) is configured to deliver an electrical charge (605) to a person (601) in cardiac distress. The compact automated external defibrillator (100) is further configured to support a plurality of cardiac rescues because it is reusable on another person (601), preferably after the first distal-foam pad (460), AED first-distal electrode (115), and AED first-distal pad (410) are removed and replaced, and also after the AED proximate pad (405) and the liner (335) have been removed and replaced.

The compact automated external defibrillator (100) includes a device body (105) that houses the components of the compact automated external defibrillator (100), which may be referred to herein as the AED. The AED operationally functions using a circuit board (415) within the device body (105) that permits a battery (450) also within the device body (105) to energize both electrodes. The battery (450) is preferably lodged at the base of the device body (105) on its front side, which is shown in FIG. 4 on the right of the exploded view and within a front-body housing (445). Preferably, the battery (450) is not part of, or mounted to, the circuit board. The rear cover (465) is shown to the left-side of the exploded view of the device body (105) in FIG. 4.

The device body (105) contains a proximate electrode (110) and an AED first-distal electrode (115). The proximate electrode (110) is an integrated part of the device body (105). It is preferably supplemented by an AED proximate pad (405), which is preferably made of an electrically conducting adhesive gel, such as hydrogel. If hydrogel is not used, the AED proximate pad (405) may include a skin adhesive (905) that is made to stick to the skin of a person (601) in cardiac distress. An electrode adhesive (910) may be applied to adhere the AED proximate pad (405) to the proximate electrode (110).

The AED proximate pad (405) is electrically conductive and is thus able to conduct the electrical charge (605) to or from the proximate electrode (110).

The AED proximate pad (405) is preferably the larger of the two pads. The AED proximate pad (405) is connected to the AED by adhering or fastening to the device body (105). The AED proximate pad (405) and the AED first-distal pad (410) are preferably made of hydrogel. The term "pad" is used loosely in this sense that the AED proximate pad (405) and the AED first-distal pad (410) may be formed simply by applying hydrogel adhesive in lines, dashed lines, or lots of tiny dots. In practice, the substance forming the AED proximate pad (405) and the AED first-distal pad (410) may not be considered by some to be a pad in the traditional sense of it being a thick piece of soft material. Hydrogel or another adhesive may be similarly applied to the connecting electrode (130) and insulating cover (432). The connecting electrode (130) is preferably tin or silver.

Thus, the device body (105) is configured to operably integrate with the proximate electrode (110). To facilitate reuse of the AED with new adhesive pads, the AED proximate pad (405) is a removable part of the proximate electrode (110) and also a removable part of the device body (105). The proximate electrode (110) is restored to near-new condition by peeling off the used AED proximate pad (405) and adhering a new replacement pad to the proximate electrode (110). The AED proximate pad (405), liner (335), AED first-distal pad (410), AED first-distal electrode (115), first distal-foam pad (460), and packing cover (455) may also be removed and replaced should that become necessary for any reason.

The AED first-distal electrode (115) is configured to be easily unpacked from the device body (105) to deploy on the person (601) in cardiac distress. Preferably, a liner (335) is placed between the two electrodes so that the AED first-distal electrode (115) can be easily separated from the proximate electrode (110) and unpacked from the device body (105). More precisely, in a preferred embodiment, the liner (335) is placed between the AED proximate pad (405) and the AED first-distal pad (410) to keep them from sticking together when separated during an emergency. The liner (335), the AED proximate pad (405), AED first-distal electrode (115), AED first-distal pad (410), first distal-foam pad (460), packing cover (455), wire (120), and insulating cover (432) are user replaceable. In another embodiment, a second liner is provided on the other side of the AED proximate pad (405) prior to installation onto the proximate electrode (110) to aid in shipping and packaging the AED proximate pad (405). This second liner faces the proximate electrode (110) and is removed from the AED proximate pad (405) prior to installation on the proximate electrode (110).

In an alternative embodiment, the AED first-distal electrode (115), the proximate electrode (110), or the connecting electrode (130) can made of a carbon-loaded vinyl, which is an electrically conductive material and can serve as a substitute for tin or silver.

In another alternative embodiment, the AED first-distal electrode (115) is twice the size of the pad geometry and then folded over on itself with the splayed wire strands between the layers of AED first-distal electrode (115). A layer of electrode adhesive (910) holds together the strands (125) of the wire (120) and the folded AED first-distal electrode (115). The benefit of this embodiment is that it provides a higher level of surface area between the AED first-distal electrode (115) and the strands (125).

Figure 2:
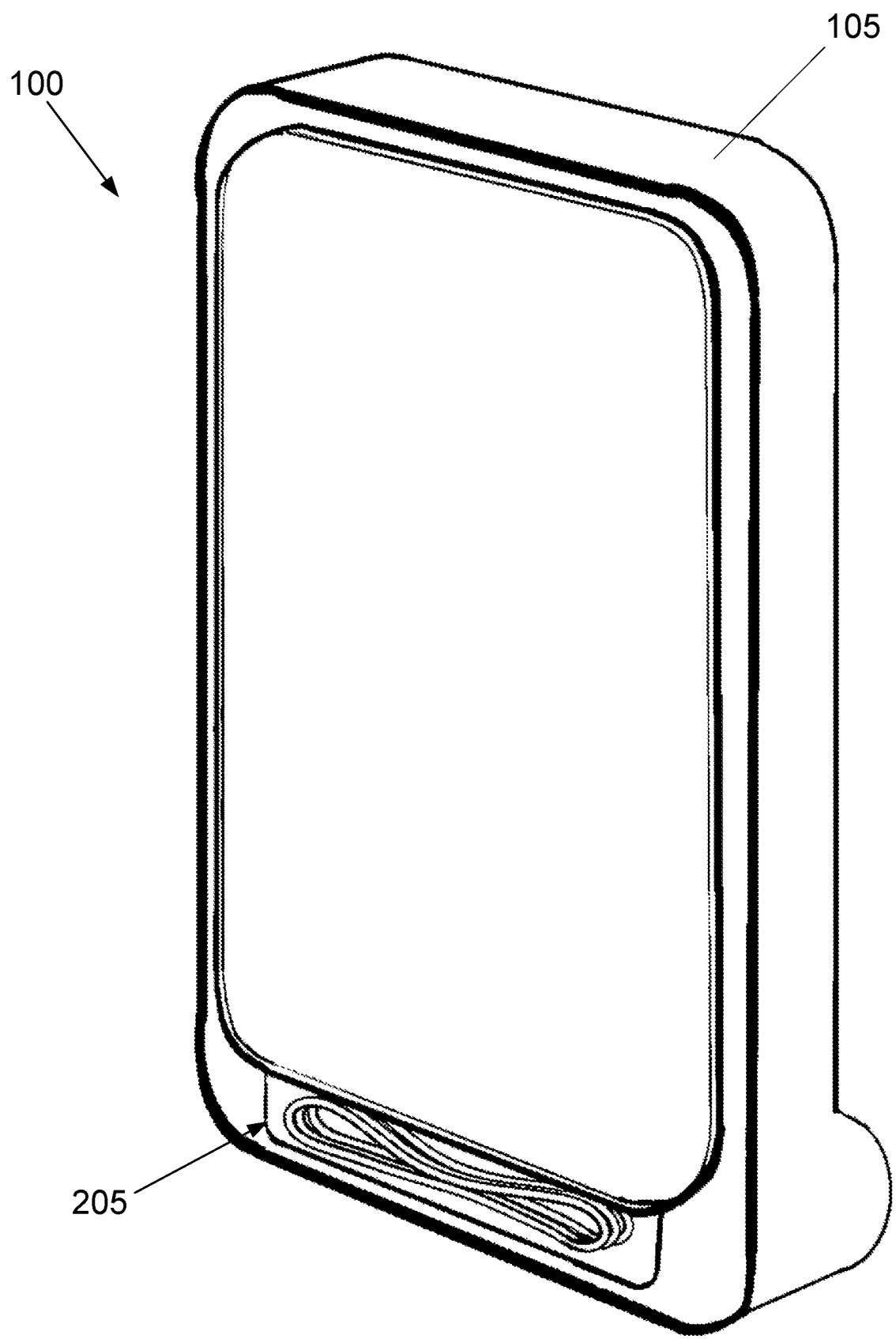
FIG. 2 is a perspective view of the first embodiment of the compact AED with integrated CPR coaching without a rear cover.

The AED first-distal electrode (115) does not require a typical electrical connector like other AEDs (such as a plug), makes contact to the connecting electrode (130) on the device body (105) of the AED, and only requires a single wire or cord. The wire (120) preferably stores in a carve-out (205) toward the rear of the device body immediately to the front of where the rear cover (465) would go when added to device body shown in FIG. 2.

Most commonly, the gel used for AED electrodes is typically an adhesive gel, such as hydrogel. Typically, no other adhesive coating is needed with this type of gel. Optionally, the AED proximate pad (405) may be coated with one or more adhesives on each side of the AED proximate pad (405) for attachment to the proximate electrode (110) and for attachment to the person (601) once the AED first-distal electrode (115) is unpacked. While the adhesive may be used at different locations within the AED and may be the same adhesive in composition, each adhesive at a different location is given a distinct name to accommodate the potential for different adhesives being used and to avoid confusion. The adhesive that sticks to a person's skin is referred to as a skin adhesive (905). The adhesive used to stick the AED proximate pad (405) to the proximate electrode (110), to stick the AED first-distal pad (410) to the AED first-distal electrode (115), and to stick an insulating cover and a wire (120) to the connecting electrode (130) is referred to as an electrode adhesive (910). Finally, the adhesive used to seal the device body (105) from air infiltration is referred to as the adhesive (320), which is preferably a silicone adhesive.

The AED first-distal electrode (115) is electrically connected from the device body (105) by a wire (120). The wire (120) must be of sufficient gauge and otherwise configured to deliver the electrical charge (605) to the AED first-distal electrode (115) from the device body (105). The AED first-distal electrode (115) is configured to be replaceable and further configured to be operable by the circuit board (415) in the device body (105). No other circuit board positioned outside the device body, for example, one in or on the distal electrode is needed. Preferably, the AED first-distal electrode (115) is configured to be exclusively operable by the circuit board (415) in the device body (105).

Preferably, the circuit board (415) in device body (105) of the compact automated external defibrillator (100) is configured to deliver a reversal of the electrical polarity of the electrical charge (605) during the time the AED is delivering a charge to the person (601). This is termed a biphasic charge or shock. With any biphasic shock, the direction of current flow is reversed during the electrical defibrillation cycle. In the preferred embodiment of the compact automated external defibrillator (100), such reversal is implemented at least one time while delivering the electrical charge (605).

Preferably, the circuit board (415) is configured to be an indivisible unit within the device body (105). This means that the circuit board (415) is not separable into two or more circuit board components. While there may be more than one printed circuit board (PCB) within the device body (105), none such PCB may be broken off from another PCB and preferably, none is located in the AED first-distal electrode (115).

The compact automated external defibrillator (100) preferably employs the AED proximate pad (405) on the device body (105) so that the AED proximate pad (405) may be peeled off the device body (105). While an electrical plug provides a relatively easy means for disconnecting any electrical component, the preferred connection for the proximate electrode (110) to the circuitry within the device body (105) is one involving electrical contact with the circuit board. A clip, a fastener, hydrogel and/or an adhesive may be employed to secure this contact.

The compact automated external defibrillator (100) is preferably configured with the wire (120) composed of strands (125) of smaller diameter wires. The strands (125) are attached to the device body (105) after splaying the strands (125) on a terminal or connecting electrode (130) on the device body (105). The strands (125) may be embedded in a hardened, electrically conducting gel (431), preferably hydrogel, to make adhesion to the connecting electrode (130) easier for replacement. This arrangement is shown in FIG. 4 where the splayed wires are embedded in a hardened, electrically conducting gel (431), such as hydrogel, which can then be adhered to the connecting electrode (130). For that arrangement, there is preferably an insulating cover (432) over the gel and wires to insulate them. Because the AED first-distal electrode (115) and the proximate electrode (110) have separated electrical connections a biphasic shock is made possible. The wire (120) that connects the AED first-distal electrode (115) to the device body (105) is preferably splayed to flatten or minimize the height or profile of the connections.

In another alternative embodiment, the strands (125) that are embedded in a hardened, electrically conducting gel (431) are adhered to carbon-loaded vinyl, tin, or silver with electrode adhesive (910) which may be the same material as the hardened, electrically conducting gel (431). The carbon-loaded vinyl, tin or silver is covered with the insulating cover (432).

In another alternative embodiment, the strands (125) that are embedded in a hardened, electrically conducting gel (431) are folded between a carbon-loaded vinyl, tin, or silver, which are electrically conductive materials. The hardened, electrically conducting gel (431) and the strands (125) are adhered to the carbon-loaded vinyl, tin, or silver with an electrode adhesive (910), which may be the same material as the hardened, electrically conducting gel (431). The carbon-loaded vinyl, tin or silver is covered with the insulating cover (432).

Similarly, the wire connection at the other end of the wire (120) on the AED first-distal electrode (115) may use splayed strands. The wire (120) is preferably attached to the AED first-distal electrode (115) after splaying its strands (125) on the AED first-distal electrode (115).

The AED first-distal electrode (115) preferably comprises a metal conductor (preferably tin or silver) with an AED first-distal pad (410) on one side next to the liner (335) adhered to the metal conductor and a first distal-foam pad (460) covering the other side of the metal conductor next to a packing cover (455). Preferably, the first distal-foam pad (460), the AED first-distal electrode (115), and the AED first-distal pad (410) is a unit. Once used, this unit is disconnected and discarded, along with the wire and a new unit is installed with a new wire. In another embodiment, the AED first-distal pad (410) is configured to be peeled off and removed from the AED first-distal electrode (115) when a replacement distal pad is needed. In addition, the AED first-distal electrode (115) is configured to be disconnected from the connecting electrode (130) at the device body (105). For example, this may be accomplished by peeling off the wire (120) and hydrogel from the connecting electrode (130), by removing the wire (120) from the connecting electrode (130), by unplugging from the device body (105), or by any other means. In an alternative embodiment, the proximate electrode (110) can also be disconnected from the device body when an electrical plug is not present, such as when it may need to be replaced for maintenance, in the event is it combined with the AED proximate pad (405), or any other reason. In yet another embodiment, the connecting electrode can also be disconnected from the device body when an electrical plug is not present, such as when it may need to be replaced for maintenance, in the event is it combined with the insulating cover (432), or any other reason.

The device body (105) is configured to store the proximate electrode (110) separated from the AED first-distal electrode (115) by a liner (335). The liner (335) is preferably a thin plastic sheet that can be easily pulled off both electrodes to free them from their storage position. Thus, the device body (105) is preferably configured to store the proximate electrode and the AED first-distal electrode (115) within the device body (105) separated by the liner (335).

The liner (335) is preferably configured to define a hole (425) through which an electrical connection is made between the pads on the proximate electrode (110) and the AED first-distal electrode (115) enabling activation of a check on the operability of a discharge circuit. This electrical connection facilitates periodic testing of the AED pads, for example the hydrogel, by the compact automated external defibrillator (100) when activated to do a simple connectivity test. Doing this would validate that the user has correctly stored the pads and that the electrical path is valid (i.e., the hydrogel has not dried out).

The discharge circuit is an electrical path from the device body (105) that houses the proximate electrode (110), through the hole (425) to the AED first-distal electrode (115), and back through the wire (120). In an alternative embodiment, the discharge circuit is an electrical path from the device body (105) through the wire (120) to the AED first-distal electrode (115), through the hole (425), to the proximate electrode (110).

When in use, the circuit board (415) is configured to deliver the electrical charge (605) through the connecting electrode (130), through the wire (120) through the AED first-distal electrode (115) where the electrical charge (605) passes through the person (601) and ends at the proximate electrode (110). When a biphasic charge is employed, the circuit board (415) is also configured to deliver the electrical charge (605) through the proximate electrode (110), through the person (601), through the AED first-distal electrode (115), through the wire (120), and end at the connecting electrode (130). In other embodiments of a biphasic shock, the first electrical path may begin with the proximate electrode and then switch to the distal electrode.

Figure 7:
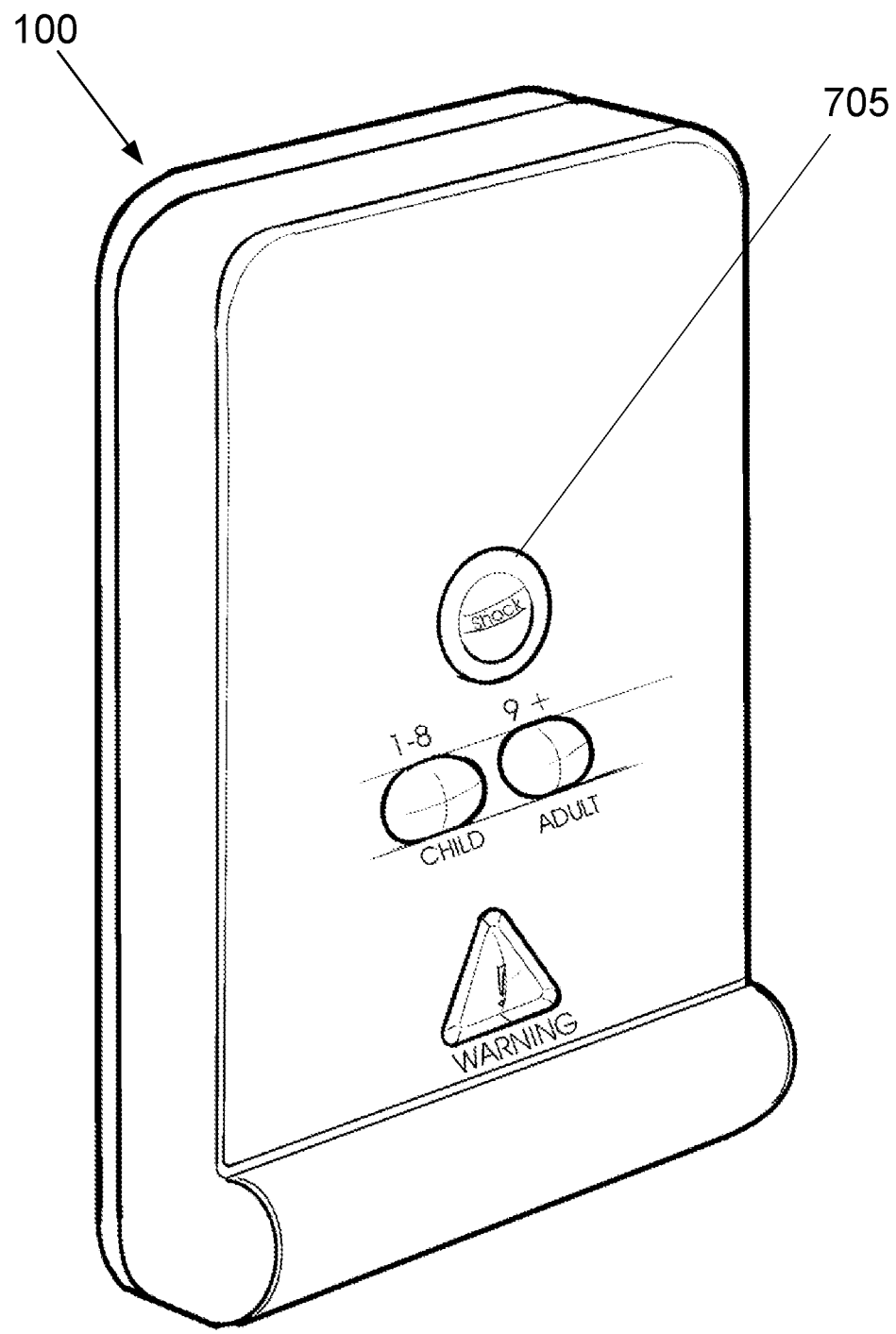
FIG. 7 is a perspective view of the front of an embodiment of the compact AED.

As an example, FIG. 7 shows an activation button (705) along with other controls on the front face of the compact automated external defibrillator (100). In this embodiment, the activation button (705) enables use of the AED to send the electrical charge (605) through the person (601). Other embodiments include automatic activation of the AED, for example when an arrhythmia is detected.

Figure 3:
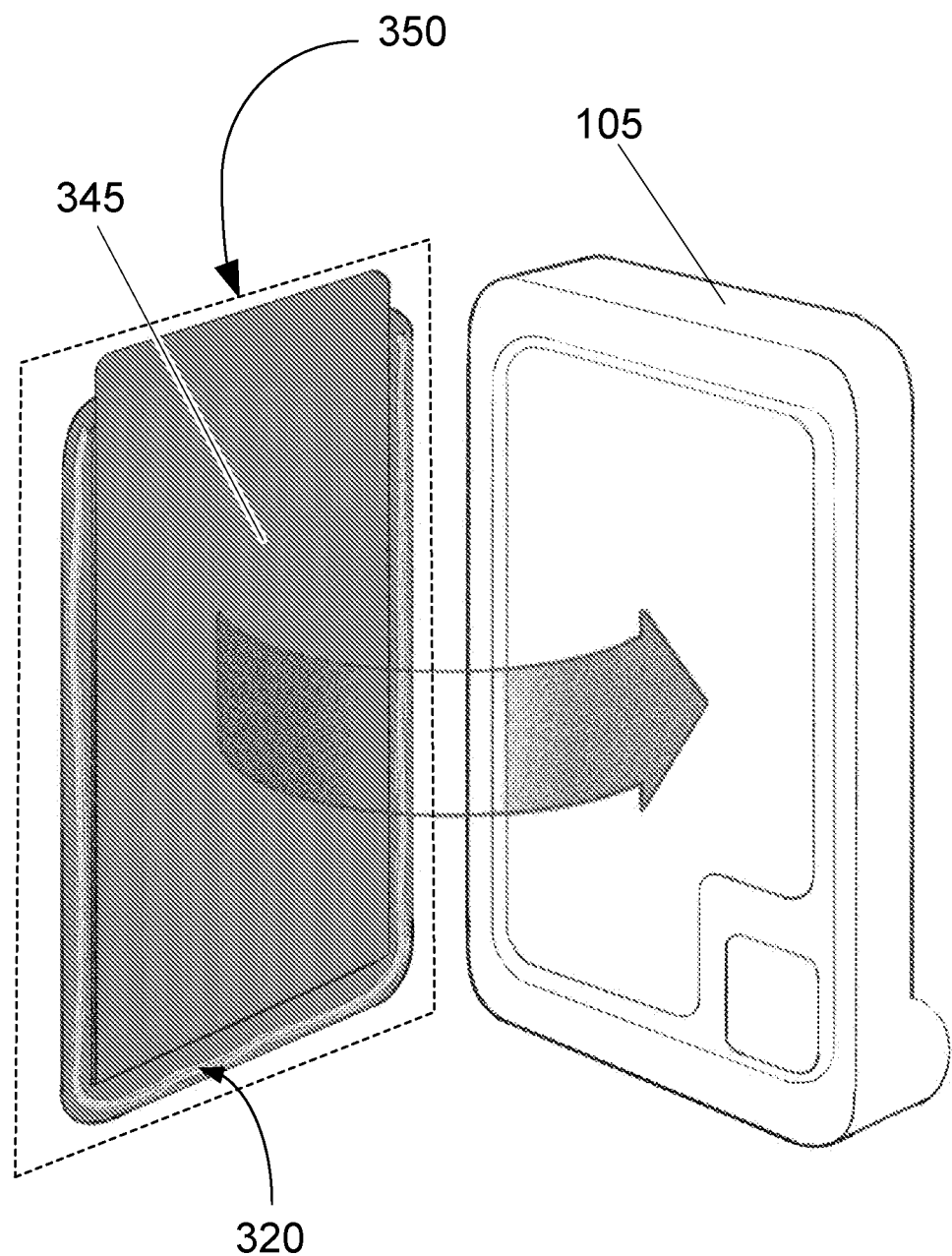
FIG. 3 is a perspective view of the first embodiment of the compact AED with integrated CPR coaching and showing a packaging envelope.

A packaging envelope (350) is shown in FIG. 3 within the rectangular dashed box. A pull-tab (345) may be used to unseal the packaging envelope (350). The packaging envelope (350) is configured to seal the AED proximate pad (405) and AED first-distal pad (410) to help keep them or prevent them from drying out when in storage, and the pull-tab (345) is configured to easily open the packaging envelope (350) during a rescue in order to reveal the AED proximate pad (405) and align it to the proximate electrode (110).

A metalized surface (420) on the device body (105) may be applied to help seal the device body (105) from air entering and leaving the device body (105). Among other benefits, the metalized surface (420) prevents the pads from drying out. Thus, the metalized surface (420) is configured to seal the device body (105) when the components of the AED are in storage.

Figure 8:
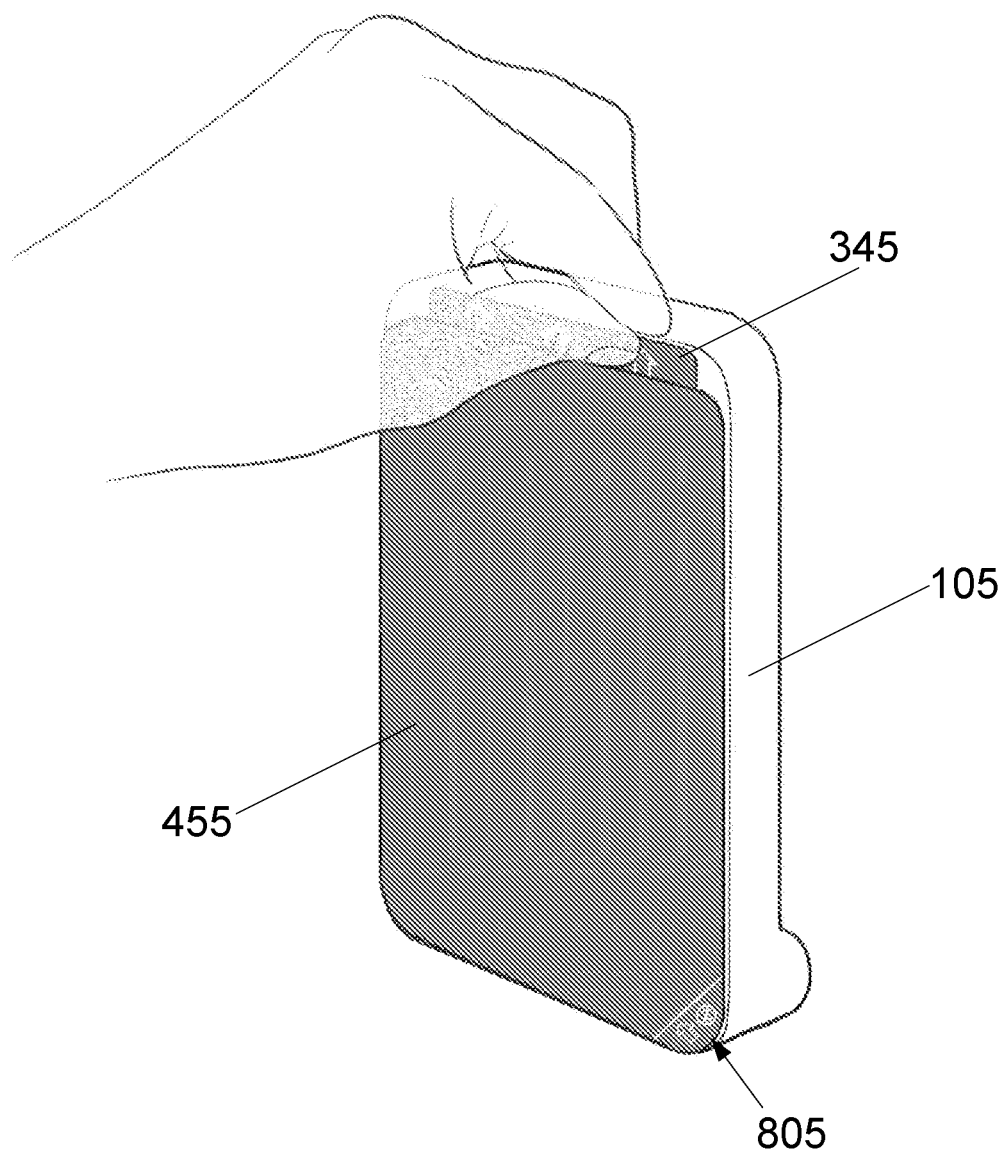
FIG. 8 is rear view of the front-body housing of an embodiment of the compact AED with a packing cover over a packaging envelope with a pull-tab.
Figure 9:
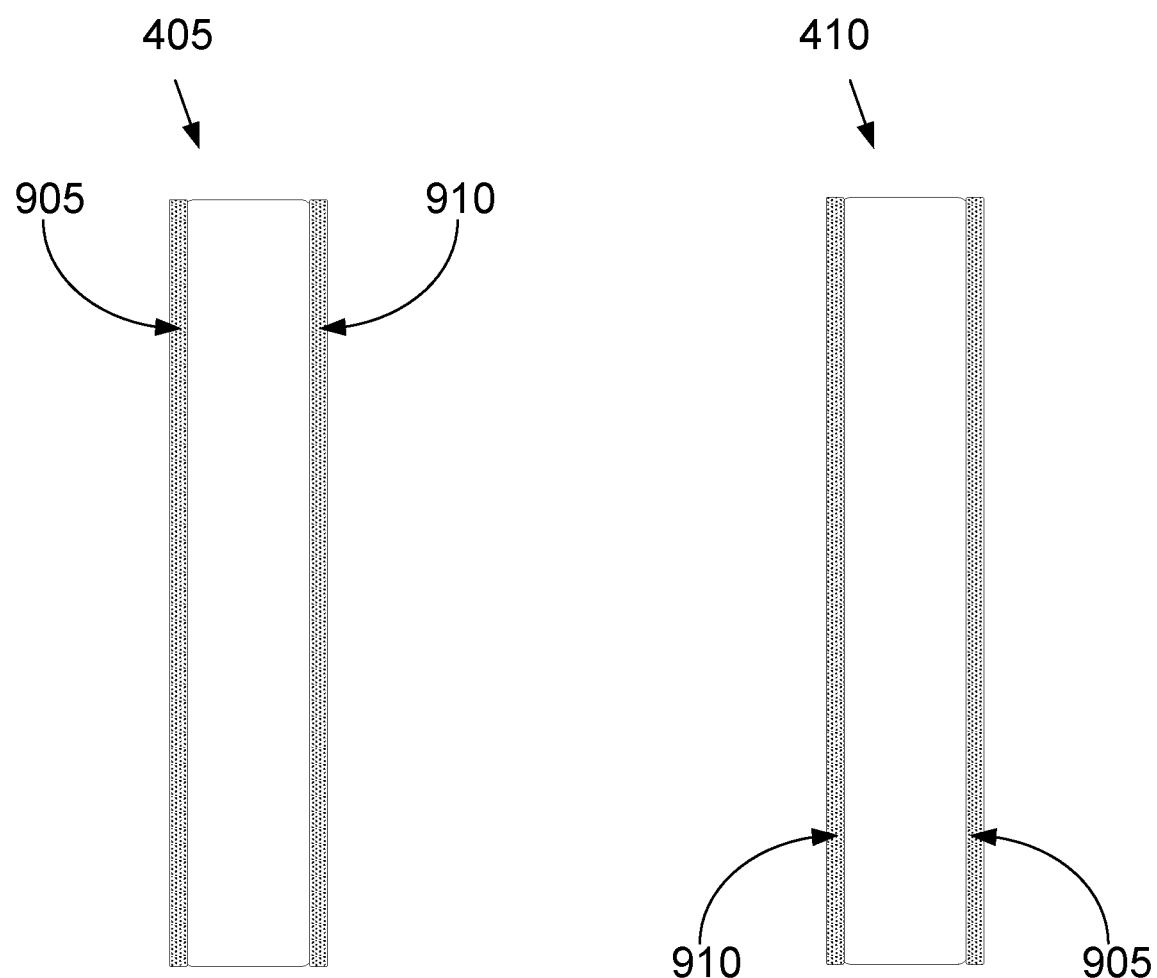
FIG. 9 is a side view of the proximate pad and the distal pad showing the skin adhesive and the electrode adhesive.

As shown in FIG. 4, a rear cover (465) is a rigid closure for the device body (105). The rear cover (465), for example, could be a hard plastic. An adhesive (320), such as silicone, may be used on the periphery of the packaging envelope (350) to engage with the device body (105). Additionally, a packing cover (455) may be included to help seal up the device body (105) when the components are stored therein. The packing cover (455), like the rear cover (465), is preferably made of a light weight material, such as plastic, foam, or that is metalized material. For example, a metalized coating or seal would be peeled away at the corner or edge of the device. A peelable corner tab (805) is shown in FIG. 8 for the lower right-hand corner of the packing cover (455).

In an alternative embodiment, the packing cover (455) may serve to replace the first distal-foam pad (460), revealing the AED first-distal electrode (115) and AED first-distal pad (410) underneath of it once removed.

Figure 10:
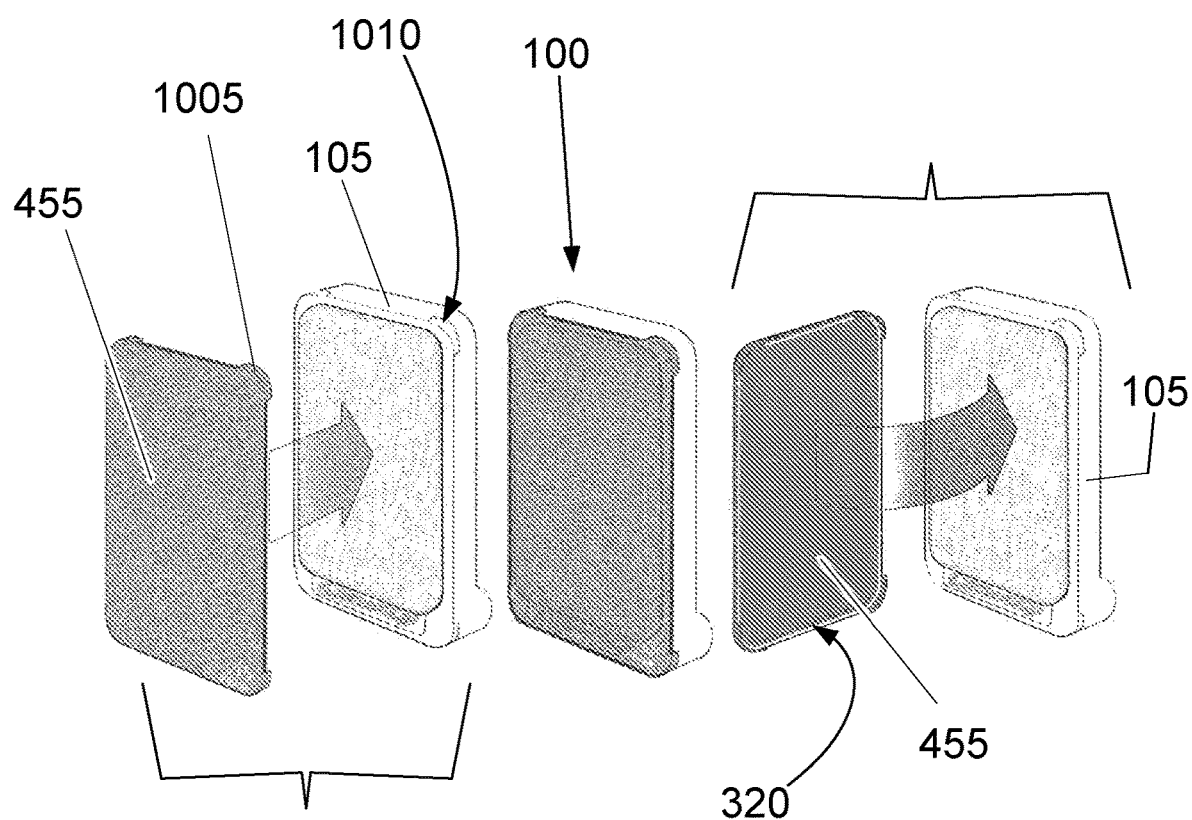
FIG. 10 is an exploded view of an alternative embodiment where the rear cover and packing cover are combined, to comprise a plastic that has an adhesive around the periphery to seal to the device body.

In an alternative embodiment shown in FIG. 10, the rear cover (465) may be combined with the packing cover (455), designated packing cover (455) in FIG. 10. The packing cover (455) is composed of plastic and is sealed to the device body (105) with adhesive (320) around the periphery of the packing cover (455). The adhesive (320) is preferably silicone adhesive. In another embodiment, the packing cover (455) may be configured with a corner clip (1005), preferably 4 corner clips at each corner of the packing cover (455). Such clips may also be present on the rear cover (465) and the rear cover (465) itself may also be sealed to the device body with adhesive (320). Preferably, each corner clip (1005) mates with a notch (1010) on the device body (105), which ensures a tight fit, and a seal by the adhesive (320). The plastic of the packing cover (455) may seal against a metalized surface on the device body (105) to help prevent air infiltration.

In another embodiment, the rear cover (465) may be configured with a mechanism, such as a notch or clip, to mate with a mechanism on the device body (105), such as a notch or clip, to ensure proper orientation of the connecting electrode (130).

In another alternative embodiment, the packing cover (455) may serve to replace the rear cover (465), revealing the distal assembly, namely the first distal-foam pad (460), AED first-distal electrode (115) and AED first-distal pad (410), underneath of it once removed. Adhesive sealant around the inside of the packing cover (455) connects to the device body (105) and prevents air infiltration to the pads.

In sum, important component parts of the compact automated external defibrillator (100) include: the first distal-foam pad (460), the AED first-distal electrode (115), and the AED first-distal pad (410), which are an assembly, and which adhere to the person in cardiac distress; the electrodes, including the AED first-distal electrode (115) and the proximate electrode (110), which are conductive metals, preferably tin or silver, which form the conductive portion that connect to the person in cardiac distress and also the AED first-distal electrode (115) is the component that connects to the wire (120) that then connects to the device body (105); the AED first-distal pad (410) and the AED proximate pad (405), which are preferably made of hydrogel and which include an electrically conductive gel that adheres each electrode to the patient and that creates a lower resistance electrical path to the patient; the proximate electrode (110) and the AED first-distal electrode (115), which are electrically conductive elements that are connected to AED's internal circuitry.

The above-described embodiments including the drawings are examples of the compact automated external defibrillator (100) and merely provide illustrations of the compact automated external defibrillator (100). Other embodiments will be obvious to those skilled in the art. Thus, the scope of the compact automated external defibrillator (100) is determined by the appended claims and their legal equivalents rather than by the examples given.

INDUSTRIAL APPLICABILITY

The compact automated external defibrillator (100) has application to the medical industry.

What is claimed is:

1. A compact automated external defibrillator configured to provide coaching on cardiopulmonary resuscitation (CPR) for a person in cardiac distress and further configured to deliver an electrical charge to the person, the compact automated external defibrillator comprising:
a device body, the device body comprising a front-body housing and a user-separable cartridge;
the front-body housing configured to be used for CPR performance improvement, the front-body housing comprising:
a front surface facing outward;
a sensor configured to measure and report on CPR being performed on the person, the sensor configured for operability when the front surface is laid atop the person;
a circuit board configured as an indivisible unit;
a wall that secures the circuit board within the front-body housing;
at least two separate and reusable terminals defined on the wall;
the at least two separate and reusable terminals electrically connected to the circuit board;
the at least two separate and reusable terminals forming connections for electrodes, the electrodes configured for use in delivering an electrical charge for defibrillation; and
the at least two separate and reusable terminals become accessible upon removing the user-separable cartridge from the device body; and
the user-separable cartridge comprises at least two separated cartridge terminals defined on a second wall, each of the at least two separated cartridge terminals configured to electrically connect to one of the at least two separate and reusable terminals.

2. The compact automated external defibrillator of claim 1, wherein the user-separable cartridge comprises: an AED proximate pad; a liner; an AED first-distal pad; an AED first distal-foam pad; and an AED first-distal electrode.

3. The compact automated external defibrillator of claim 2, wherein the AED proximate pad is configured to attach the user-separable cartridge to the person.

4. The compact automated external defibrillator of claim 2, wherein the AED proximate pad is configured for removal from the user-separable cartridge while maintaining an electrical connection to a first of the at least two separate and reusable terminals, and the AED proximate pad is further configured for attachment to the person to enable electrical current flow between the AED proximate pad and the person.

5. The compact automated external defibrillator of claim 2, wherein the user-separable cartridge further comprises a packing cover.

6. The compact automated external defibrillator of claim 2, wherein the user-separable cartridge is disposable, said user-separable cartridge configured for replacement.

7. The compact automated external defibrillator of claim 2, wherein the user-separable cartridge further comprises a second distal-foam pad.

8. The compact automated external defibrillator of claim 1, wherein the AED first-distal electrode is electrically connected to a first of the at least two separated cartridge terminals.

9. The compact automated external defibrillator of claim 1, wherein the user-separable cartridge further comprises an AED second-distal electrode configured for attachment to the AED proximate pad.

10. The compact automated external defibrillator of claim 9, wherein the AED second-distal electrode is electrically connected to a second of the at least two separated cartridge terminals.

11. The compact automated external defibrillator of claim 1, wherein the sensor is configured to measure acceleration of a person's chest.

12. The compact automated external defibrillator of claim 1, wherein the sensor is configured to measure force applied to the person.

13. The compact automated external defibrillator of claim 1, wherein a first of the at least two separate and reusable terminals is a proximate electrode.

14. The compact automated external defibrillator of claim 1, wherein the circuit board is configured for defibrillation and further configured to calculate rate of CPR using data from the sensor.

15. The compact automated external defibrillator of claim 1, wherein the circuit board is configured for defibrillation and further configured to calculate depth of CPR using data from the sensor.

16. The compact automated external defibrillator of claim 1, further comprising a speaker connected to the circuit board, the circuit board configured to provide instruction through the speaker using data from the sensor.

17. The compact automated external defibrillator of claim 1, wherein the circuit board is configured to redact CPR compression artifacts from an electrocardiogram using data from the sensor.

* * * * *